United States Patent
Bacus et al.

(10) Patent No.: US 10,851,422 B2
(45) Date of Patent: Dec. 1, 2020

(54) METHODS OF DETERMINING AN IMMUNE RESPONSE SCORE

(71) Applicant: American Molecular Laboratories Inc., Vernon Hills, IL (US)

(72) Inventors: Sarah S. Bacus, Hinsdale, IL (US); Christopher A. Hamm, Chicago, IL (US)

(73) Assignee: American Molecular Laboratories Inc., Vernon Hills, IL (US)

( * ) Notice: Subject to any disclaimer, the term of this patent is extended or adjusted under 35 U.S.C. 154(b) by 10 days.

(21) Appl. No.: 15/705,571

(22) Filed: Sep. 15, 2017

(65) Prior Publication Data
US 2018/0080087 A1 Mar. 22, 2018

Related U.S. Application Data

(60) Provisional application No. 62/396,349, filed on Sep. 19, 2016.

(51) Int. Cl.
*C12Q 1/6886* (2018.01)
*G01N 33/574* (2006.01)

(52) U.S. Cl.
CPC ......... *C12Q 1/6886* (2013.01); *G01N 33/574* (2013.01); *G01N 33/57423* (2013.01); *C12Q 2600/106* (2013.01); *C12Q 2600/158* (2013.01)

(58) Field of Classification Search
CPC .................................................. C12Q 1/6886
USPC ....................................................... 424/133.1
See application file for complete search history.

(56) References Cited

U.S. PATENT DOCUMENTS 8,747,867 B2 * 6/2014 Di Fiore .............. C12Q 1/6886
424/277.1

OTHER PUBLICATIONS

Tockman et al (Cancer Res., 1992, 52:2711s-2718s).*
Choueiri et al (Clin Cancer Res, 2016, 22(22): 5461-5471).*
Brahmer et al (NEJM, 2015, 373(2): 123-135).*

* cited by examiner

*Primary Examiner* — Sean E Aeder
(74) *Attorney, Agent, or Firm* — Christopher J. Betti; Morgan, Lewis & Bockius LLP

(57) ABSTRACT

The present disclosure provides method for determining an immune response score (irScore), the method comprising: determining a number of differentially expressed genes that have are implicated in anti-tumor immune cell signaling/activation; determining a number of differentially expressed genes that are implicated in immunosuppression, wherein the irScore=$X^{(low,\ medium,\ or\ high)}$, wherein X is the number of differentially expressed genes that are implicated in anti-tumor immune cell signaling/activation, and wherein low refers to 1-4 differentially expressed genes that are implicated in immunosuppression, medium refers to 5-9 differentially expressed genes that are implicated in immunosuppression, and high refers to 10 or more differentially expressed genes that are implicated in immunosuppression.

10 Claims, 2 Drawing Sheets

Immunostaining CD8 in NSCLC: Aggregating CD8 cells

Immunostaining CD8 in NSCLC: No Aggregating CD8 cells

Dual Immunostaining reveals PD-L1 expressing NSCLC cells surrounded by CD8+ immune cell aggregates.

METHODS OF DETERMINING AN IMMUNE RESPONSE SCORE

FIELD

The present disclosure relates generally to methods for determining an immune response score (irScore).

BACKGROUND

Recent advances in the understanding of the relationship between a subject's immune system and tumor progression have led to the development of drugs (immunotherapies) that exploit the immune system to treat cancer.

Immunotherapies effectively treat cancer by exploiting the fact that tumors typically harbor mutant proteins or other molecules that may be recognized as antigens by the immune system. Using these cancer antigens as targets, immunotherapy provokes the immune system into attacking tumor cells. Immunotherapies come in many forms including vaccines (cancer specific proteins or cells that are administered to patients to stimulate an immune response), monoclonal antibodies (antibodies specific to tumor proteins that bind to cancer cells and attract immune cells to attack the tumor), biological response modifiers (proteins such as cytokines used to increase immune response to attack cancer cells), and cellular immunotherapy (immune cells removed from the body that are activated and grown in a lab prior to returning to patient where they attack the cancer). However, not all patients respond to immunotherapy and as such biomarkers of response and resistance to immunotherapies are of great importance in the stratification of patients to receive these therapies.

Analysis of immune cell infiltrates in tumors is typically performed by immunohistochemical (IHC) staining. However, the inherent complexity of IHC analysis, in conjunction with protocol variability, analysis of different immune cell types, inconsistent tissue region selection criteria, dramatic intra-tumoral heterogeneity of immune infiltrates combined with differences in conjunction with qualitative and semiquantitative criteria to measure immune infiltration, all contribute to the variability of the results obtained, and raise the concern that specialized protocols and training may be required. Therefore, more accurate techniques are desired to create a more uniform assay to indicate levels of immune cell infiltration thereby avoiding the inherent limitations of current IHC-based approaches.

SUMMARY

The present disclosure generally relates to methods for determining an immune response score (irScore). an immune response score (irScore) may be determined by a method comprising: obtaining a biological sample; determining a number of expressed genes that are implicated or known to be involved in anti-tumor immune cell signaling/activation in the biological sample (e.g., the genes set forth in Table 1 or the subset of genes set forth in Table 2); determining a number of expressed genes that are implicated in immunosuppression in the biological sample (e.g., the genes set forth in Table 1 or the subset of genes set forth in Table 2), wherein the irScore=$X^{(low,\ medium,\ or\ high)}$, wherein X is the number of expressed genes that are implicated in anti-tumor immune cell signaling/activation, and wherein low refers to 1-4 expressed genes that are implicated in immunosuppression, medium refers to 5-9 expressed genes that are implicated in immunosuppression, and high refers to 10 or more expressed genes that are implicated in immunosuppression.

In some embodiments, the determination of an irScore can be used to assess whether or not a subject will or will not respond to treatment with an anticancer immunosuppressive agent such as Nivolumab, Pembrolizumab, Aezolizumab, Durvalumab, Avelumab, Ipilimumab, or Tremelimumab.

In some embodiments, the expressed genes that are implicated or known to be involved in anti-tumor immune cell signaling/activation are selected from those genes set forth in Table 1 or the subset of genes set forth in Table 2.

In some embodiments, the expressed genes that are implicated or known to be involved in immunosuppression are selected from those genes set forth in Table 1 or the subset of genes set forth in Table 2.

In some embodiments, the expressed genes that are implicated in anti-tumor immune cell signaling/activation are selected from those genes set forth in Table 1 or the subset of genes set forth in Table 2 and wherein the expressed genes that are implicated in immunosuppression are selected from those genes set forth in Table 1 or the subset of genes set forth in Table 2.

The present disclosure also provides a method for treating a subject with an anticancer immunotherapy, the method comprising: obtaining a biological sample from the subject; determining an immune response score (irScore) for the biological sample as provided herein; and treating the subject with the immunotherapy where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$ or $25^{low}$ or greater, $6^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the iummunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{hi}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater.

In some embodiments, the subject is a cancer patient.

In some embodiments, the anticancer immunotherapy is Nivolumab (Opdivo; Bristol Myers; PD-1 inhibitor), Pembrolizumab (Keytruda; Merck; PD-1 inhibitor), Atezolizumab (Tecentriq; Roche; PD-L1 inhibitor), Durvalumab (Astra Zeneca; PD-L1 inhibitor), Avelumab (Pfizer; PD-L1 inhibitor), Ipilimumab (Yervoy; Bristol Myers; CTLA4 inhibitor), or Tremelimumab (Astra Zeneca; CTLA4 inhibitor).

In some embodiments, the biological sample is non-small cell lung cancer (NSCLC).

In some embodiments, the irScore is determined by: obtaining a biological sample; determining a number of expressed genes that have are implicated in anti-tumor immune cell signaling/activation in the biological sample; determining a number of expressed genes that are implicated in immunosuppression in the biological sample, wherein the irScore=$X^{(low,\ medium,\ or\ high)}$, wherein X is the number of expressed genes that are implicated in anti-tumor immune cell signaling/activation, and wherein low refers to 1-4 expressed genes that are implicated in immunosuppression, medium refers to 5-9 expressed genes that are implicated in immunosuppression, and high refers to 10 or more expressed genes that are implicated in immunosuppression.

The present disclosure also provides a method for predicting whether a subject will respond to treatment with an anticancer immunotherapy, the method comprising: obtaining a biological sample from the subject; and determining an immune response score (irScore) for the biological sample as provided herein, wherein the subject is predicted to respond to the anticancer immunotherapy where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$, or $25^{low}$ or greater, $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the immunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater.

In some embodiments, the anticancer immunotherapy is Nivolumab (Opdivo; Bristol Myers; PD-1 inhibitor), Pembrolizumab (Keytruda; Merck; PD-1 inhibitor), Atezolizumab (Tecentriq; Roche; PD-L1 inhibitor), Durvalumab (Astra Zeneca; PD-L1 inhibitor), Avelumab (Pfizer; PD-L1 inhibitor), Ipilimumab (Yervoy; Bristol Myers; CTLA4 inhibitor), or Tremelimumab (Astra Zeneca; CTLA4 inhibitor).

The present disclosure also provides a method for characterizing an immune-tumor microenvironment, the method comprising: obtaining biological samples; classifying the biological samples into a high immune infiltration group or a low immune infiltration group based on a level of immune infiltration in the sample; generating gene expression values for the biological samples with high levels of immune infiltration and for the biological samples with low levels of immune infiltration; and comparing the gene expression values for biological samples with high levels of immune infiltration and biological samples with low levels of immune infiltration to determine a gene expression signature that is associated immune cell infiltration and aggregation.

In some embodiments, the biological samples are classified into a high immune infiltration group or a low immune infiltration group based on the level of immune infiltration in the sample and wherein immune infiltration is determined by immunohistochemistry.

In some embodiments, the gene expression values for the biological samples with high levels of immune infiltration and for the biological samples with low levels of immune infiltration are determined by next-generation sequencing.

In some embodiments, the biological sample is non-small cell lung cancer (NSCLC).

BRIEF DESCRIPTION OF THE FIGURES

The foregoing summary as well as the following detailed description will be better understood when read in conjunction with the appended FIGURES. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1A:
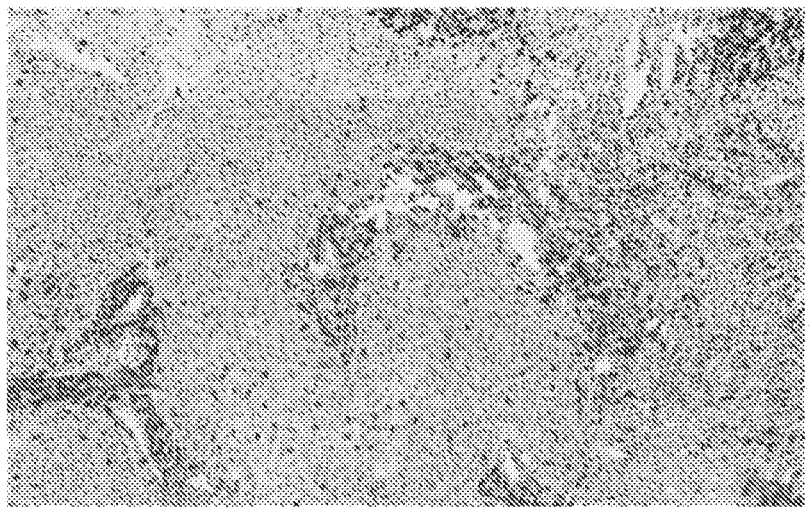
FIG. 1: Representative immuno-histochemical (IHC) staining of NSCLC tumors (Panel A) with aggregating CD8+ cells and (Panel B) without CD8+ aggregates. Dual immunostaining reveals PD-L1 expressing NSCLC cells surrounded by immune cell aggregates. CD8+ immune cells aggregate surround the tumor cells, however, PD-L1 expression may contribute to immune escape. CD8 and PD-L1 Immunostaining (20×) (Panel C).

The tumor-immune microenvironment is composed of anti-tumor immune signaling and immunosuppressive signaling, and the intensity and diversity of this signaling may be important for generating an effective immune response. Immune cell signaling is directly relevant to cancer immunotherapy since the immune cell signaling may have value in determining whether a patient will or will not respond to a particular immunotherapy. In order to predict a patient's response to immunotherapy, it is important to classify the nature of the immune response in each patient and it is important to identify the immune cell signature that is most likely to respond to a particular immunotherapy. The inventors have found that a clinical benefit from immunotherapy is defined by both the expression of genes related to anti-tumor immune cell signaling/activation, and the expression of genes that play a role in immunosuppression. This disclosure provides for the determination of an irScore for a biological sample which represents a measurement of the immunostimulatory and immunosuppressive genes in the tumor microenvironment. The irScore may be used to characterize the immune tissue microenvironment and/or predict a subject's responsiveness to anticancer immunotherapy.

The present disclosure generally relates to a method for determining an immune response score (irScore) which can be used to assess whether or not a subject will or will not respond to treatment with an anticancer immunosuppressive agent. For example, the method may comprise determining a number of expressed genes that are implicated in anti-tumor immune cell signaling/activation in a biological sample; determining a number of expressed genes that are implicated in immunosuppression in the biological sample, wherein the irScore=$X^{(low,\ medium,\ or\ high)}$, wherein X is the number of differentially expressed genes that are implicated in anti-tumor immune cell signaling/activation, and wherein low, medium, or high refers to a number of expressed genes that are implicated in immunosuppression. For example, low may refer to 1-4, 5-10, 10-20, 20-30, 30-40, or 40-50 or more expressed genes that are implicated in immunosuppression, medium may refer to 5-9, 10-20, 20-30, 30-40, 40-50, 50-60, 60-70 or more expressed genes that are implicated in immunosuppression, and high may refer to 10 or more, 20 or more, 30 or more, 40 or more, 50 or more, 60 or more, 70 or more, 80 or more, 90 or more, or 100 or more expressed genes that are implicated in immunosuppression. X may be any integer including, for example, any integer between 1-10, 10-20, 20-30, 30-40, 40-50, 50-60, 60-70, 70-80, 80-90, 90-100 or more.

The present disclosure also provides a method for treating a subject with an anticancer immunotherapy, the method comprising: obtaining a biological sample from the subject; determining an immune response score (irScore) for the biological sample; and treating the subject with the immunotherapy where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$, or $25^{low}$ or greater, $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the immunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. In a preferred embodiment, the irScore is at least $5^{medium}$, $6^{medium}$, $7^{medium}$, $8^{medium}$, $9^{medium}$, $10^{medium}$, $11^{medium}$, $12^{medium}$, $3^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the immunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$ or $25^{high}$ or greater. More preferably, the subject is treated with the immunotherapy where the irScore is at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater.

The present disclosure also provides a method for predicting whether a subject will respond to treatment with an anticancer immunotherapy, the method comprising: obtaining a biological sample from the subject; and determining an immune response score (irScore) for the biological sample as provided herein, wherein the subject is predicted to respond to the anticancer immunotherapy where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$ or $25^{low}$ or greater, $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the immunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. More preferably, the subject is treated with the immunotherapy where the irScore is at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater.

The present disclosure also provides a method for characterizing an immune-tumor microenvironment, the method comprising: obtaining biological samples; classifying each of the biological samples into a high immune infiltration group or a low immune infiltration group based on a level of immune infiltration in the sample; generating gene expression values for the biological samples with high levels of immune infiltration and for the biological samples with low levels of immune infiltration; and comparing the gene expression values for biological samples with high levels of immune infiltration and biological samples with low levels of immune infiltration to determine a gene expression signature that is associated immune cell infiltration and aggregation.

In an embodiment, sequencing analysis (e.g., next generation sequencing analysis) may be used to measure the expression of immune-related genes in a biological sample (e.g., a NSCLC tumor) and generate a gene expression profile for the biological sample. For example, a targeted immune panel of 377 genes (see, Table 1 below) or any subset of these genes (see, Table 2 below) may be used to generate a gene expression profile.

TABLE 1

Targeted RNA-seq Immune Panel Gene Summary

ABCB1
ACTB
ADA
ADORA2A
AICDA
APC
APOL3
AR
ARHGEF2
ARHGEF5
ARHGEF7
ARID1A
ARID1B
ATM
B2M
BCL2
BCL2L1
BCL6
BLM
BLNK
BRCA1
BRCA2
BTLA
CA9
CASP1
CCL1
CCL11
CCL13
CCL16
CCL17
CCL18
CCL19
CCL2
CCL20
CCL21
CCL22
CCL23
CCL24
CCL25
CCL26
CCL27
CCL28
CCL3
CCL4
CCL5
CCL7
CCL8
CCR1
CCR10

TABLE 1-continued

Targeted RNA-seq Immune Panel Gene Summary

| |
|---|
| CCR2 |
| CCR3 |
| CCR4 |
| CCR5 |
| CCR7 |
| CCR9 |
| CCT2 |
| CD14 |
| CD160 |
| CD19 |
| CD1D |
| CD2 |
| CD209 |
| CD27 |
| CD274 |
| CD276 |
| CD28 |
| CD33 |
| CD34 |
| CD38 |
| CD3D |
| CD3E |
| CD3G |
| CD4 |
| CD40 |
| CD40LG |
| CD47 |
| CD5 |
| CD63 |
| CD68 |
| CD7 |
| CD70 |
| CD80 |
| CD81 |
| CD86 |
| CD8A |
| CD8B |
| CDKN2A |
| CEACAM3 |
| CEACAM5 |
| CEACAM7 |
| CEACAM8 |
| CEBPB |
| CEBPD |
| CKMT1A |
| CKMT2 |
| CRTAM |
| CSF1 |
| CSF1R |
| CSF2 |
| CSF3 |
| CSF3R |
| CTLA4 |
| CX3CL1 |
| CX3CR1 |
| CXADR |
| CXCL1 |
| CXCL10 |
| CXCL11 |
| CXCL12 |
| CXCL13 |
| CXCL14 |
| CXCL16 |
| CXCL2 |
| CXCL3 |
| CXCL5 |
| CXCL6 |
| CXCL9 |
| CXCR1 |
| CXCR2 |
| CXCR3 |
| CXCR4 |
| CXCR5 |
| CXCR6 |
| CXCR7 |
| CXXC4 |
| DPP4 |
| EDA2R |
| EEF2 |
| EGF |
| EGFR |
| EGR1 |
| EGR2 |
| EOMES |
| EPCAM |
| ERBB2 |
| ERCC1 |
| ESR1 |
| FADD |
| FAF1 |
| FAS |
| FASLG |
| FGFR1 |
| FGFR2 |
| FGL2 |
| FLT3 |
| FOXP3 |
| GAPDH |
| GBP1 |
| GBP2 |
| GIF |
| GNLY |
| GYPA |
| GZMA |
| GZMB |
| GZMH |
| HAVCR2 |
| HIF1A |
| HLA-A |
| HLA-B |
| HLA-C |
| HLA-E |
| HPGD |
| ICAM1 |
| ICOS |
| ICOSLG |
| ID2 |
| ID3 |
| ID4 |
| IDO1 |
| IFNA1 |
| IFNA2 |
| IFNAR1 |
| IFNAR2 |
| IFNB1 |
| IFNG |
| IFNGR1 |
| IFNGR2 |
| IFNW1 |
| IFRD1 |
| IGF1 |
| IGF1R |
| IL10 |
| IL10RA |
| IL10RB |
| IL11 |
| IL11RA |
| IL12A |
| IL12B |
| IL12RB1 |
| IL12RB2 |
| IL13 |
| IL13RA2 |
| IL15 |
| IL16 |
| IL17A |
| IL17F |
| IL18 |
| IL18R1 |
| IL19 |
| IL1A |
| IL1B |
| IL1R1 |
| IL1R2 |
| IL1RAP |
| IL1RN |

TABLE 1-continued

Targeted RNA-seq Immune Panel Gene Summary

| |
|---|
| IL2 |
| IL20 |
| IL20RA |
| IL20RB |
| IL21 |
| IL22 |
| IL22RA1 |
| IL22RA2 |
| IL23A |
| IL23R |
| IL24 |
| IL27 |
| IL28B |
| IL2RA |
| IL2RB |
| IL2RG |
| IL3 |
| IL33 |
| IL3RA |
| IL4 |
| IL4R |
| IL5 |
| IL5RA |
| IL6 |
| IL6R |
| IL6ST |
| IL7 |
| IL7R |
| IL8 |
| IL9 |
| ILK |
| IRF1 |
| IRF2 |
| IRF3 |
| IRF4 |
| IRF5 |
| IRF6 |
| IRF7 |
| IRF8 |
| IRF9 |
| ITGAX |
| ITGB3 |
| ITM2A |
| KIR3DL1 |
| KITLG |
| LAG3 |
| LTBR |
| MADCAM1 |
| MAGEA1 |
| MAGEA11 |
| MAGEA4 |
| MAGEB1 |
| MAGEB2 |
| MAGEB3 |
| MAGEC1 |
| MAGEC2 |
| MAGED1 |
| MAGED2 |
| MAGEE1 |
| MAGEF1 |
| MAGEL2 |
| MAP3K7 |
| MCAM |
| MET |
| MICA |
| MICB |
| MKI67 |
| MLH1 |
| MS4A1 |
| MSH2 |
| MSH6 |
| MYC |
| MYD88 |
| NCAM1 |
| NCK1 |
| NFAT5 |
| NFATC1 |
| NFATC3 |
| NFATC4 |
| NFKB1 |
| NGFR |
| NGFRAP1 |
| NOS2 |
| OAZ1 |
| OMD |
| PDCD1 |
| PDCD1LG2 |
| PIAS1 |
| PIAS2 |
| PIAS3 |
| PMS1 |
| PMS2 |
| PPIA |
| PRDM1 |
| PRF1 |
| PTCRA |
| PTEN |
| PTGS2 |
| PTPRC |
| RAG1 |
| RIPK1 |
| RIPK2 |
| RPL11 |
| RPL19 |
| RPL4 |
| RPLP0 |
| RPS29 |
| RRM1 |
| SCYL2 |
| SCYL3 |
| SDHD |
| SELP |
| SOCS1 |
| SPP1 |
| SRGN |
| STAT1 |
| STAT2 |
| STAT3 |
| STAT4 |
| STAT5A |
| STAT5B |
| STAT6 |
| STC2 |
| TBX21 |
| TGFB1 |
| TIRAP |
| TLR1 |
| TLR2 |
| TLR3 |
| TLR4 |
| TLR5 |
| TLR6 |
| TLR7 |
| TLR8 |
| TLR9 |
| TNF |
| TNFRSF10A |
| TNFRSF10B |
| TNFRSF10C |
| TNFRSF10D |
| TNFRSF11B |
| TNFRSF14 |
| TNFRSF17 |
| TNFRSF1A |
| TNFRSF1B |
| TNFRSF21 |
| TNFRSF25 |
| TNFRSF4 |
| TNFRSF8 |
| TNFRSF9 |
| TNFSF10 |
| TNFSF11 |
| TNFSF13B |
| TNFSF14 |
| TNFSF15 |
| TNFSF8 |

TABLE 1-continued

Targeted RNA-seq Immune Panel Gene Summary

TNFSF9
TNNC2
TNNI2
TNNI3
TOP1
TOP2A
TP53
TP63
TRADD
TTF1
TUBB3
TYMS
VAV1
VCAM1
VEGFA
VTCN1

An immune panel can be used identify significant gene expression differences (e.g., statistically significant gene expression differences) between biological samples that are characterized by different tumor infiltrating lymphocyte status. For example, an immune-tumor microenvironment may be characterized in biological samples containing low to high levels of infiltrating lymphocytes (e.g., CD8+ lymphocytes) to identify significant gene expression differences. The immune panel analysis of a biological sample (e.g., a NSCLC tumor) may reveal changes in the expression of several genes that play a role in the regulation of the immune response. For example, a T-cell "activation inhibitor" is expressed at low levels in tumors with tumor infiltrating lymphocytes aggregates, but expressed at higher levels in tumors that do not contain tumor infiltrating lymphocytes aggregates. An analysis of NSCLC tumors identified a subset of genes (from the original panel of 377; see, Table 2) that can predict a response to anticancer NSCLC immunotherapy.

The targeted immune RNA-seq panel is particularly important in immunotherapy trials because it can provide a gene expression signature that characterizes both a pre- and post-treatment immune response (e.g., robust vs non-robust immune response).

In one embodiment, to calculate an irScore, a gene expression profile is created for a biological sample using a targeted RNA-seq immune panel. The irScore is calculated by determining the total number of differentially expressed genes from the RNA-seq immune panel as compared to a reference panel from a biological sample (e.g., the same type of biological sample from another patient) with a low level of immune cells (e.g., low levels of tumor infiltrating lymphocyte aggregates), with a focus on the total number of differentially expressed genes that function in anti-tumor immune cell signaling/activation. In this manner, the irScore accounts for the expression of genes that contribute to the anti-tumor immune response, and the irScore also accounts for the expression of immunosuppressive genes.

In an embodiment, a gene may be considered differentially expressed (e.g., there is a statistically significant difference in expression) when its expression is 2×, 3×, 4×, 5×, 6×, 7×, 8×, 9×, 10×, 11×, 12×, 13×, 14×, 15×, 16×, 17×, 18×, 19×, or 20× or more, greater than the expression of the gene in a reference sample.

An irScore may be calculated as follows:

$$\text{irScore} = X^{(low, \, medium, \, or \, high)},$$

where X=#of differentially expressed genes that function in anti-tumor immune cell signaling/activation, and where "low", "medium", and "high" refer to the #of differentially expressed genes that contribute to immunosuppression.

For example, low may refer to 1-4, 5-10, 10-20, 20-30, 30-40, or 40-50 or more expressed genes that are implicated in immunosuppression, medium may refer to 5-9, 10-20, 20-30, 30-40, 40-50, 50-60, 60-70 or more expressed genes that are implicated in immunosuppression, and high may refer to 10 or more, 20 or more, 30 or more, 40 or more, 50 or more, 60 or more, 70 or more, 80 or more, 90 or more, or 100 or more expressed genes that are implicated in immunosuppression. X may be any integer including, for example, any integer between 1-10, 10-20, 20-30, 30-40, 40-50, 50-60, 60-70, 70-80, 80-90, 90-100 or more.

In an embodiment, where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$, or $25^{low}$ or greater, $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, a subject is predicted to respond to an anticancer immunotherapy.

In an embodiment, where the irScore is at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. Preferably, the subject is treated with the immunotherapy where the irScore is at least $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, a subject is predicted to respond to an anticancer immunotherapy.

In an embodiment, where the irScore is at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater. More preferably, the subject is treated with the immunotherapy where the irScore is at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater, a subject is predicted to respond to an anticancer immunotherapy.

In an embodiment, the anticancer immunotherapy is used to treat oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, glioma; parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In an embodiment anticancer immunotherapy is used to treat a non-small cell lung cancer, pancreatic cancer, breast cancer, ovarian cancer, colorectal cancer, or head and neck cancer. In yet another embodiment the cancer may be a carcinoma, a tumor, a neoplasm, a lymphoma, a melanoma, a glioma, a sarcoma, or a blastoma.

In an embodiment, the anticancer immunotherapy is used to treat a carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiated carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, or hepatic adenomatosis.

Biological samples that may be used in any of the methods of the present disclosure may include tissues, cells, biological fluids and isolates thereof, isolated from a subject, as well as tissues, cells and fluids present within a subject (e.g., a patient). Preferably, biological samples comprise cells, most preferably tumor cells, that are isolated from body samples, such as, but not limited to, smears, sputum, biopsies, secretions, cerebrospinal fluid, bile, blood, lymph fluid, urine and faeces, or tissue which has been removed from organs, such as breast, lung, intestine, skin, cervix, prostate, and stomach. Biological samples may also include sections of tissues such as frozen sections taken for histological purposes.

IHC staining of biological samples (e.g., using a CD8 antibody) may be used to identify high levels (e.g., increased levels) of cytotoxic tumor infiltrating lymphocytes (TILs). For example, the expression level of a marker for TILs such as CD8 in a biological sample may be determined by immunohistochemically staining cells in the sample using a detectably-labeled agent (e.g., an antibody) specific for CD8. In a preferred embodiment, the agent is a monoclonal antibody and the detectable label is a chromogen or a fluorophore. Alternatively, any molecule that can be detectably labeled and that specifically binds to CD8 can be used in the practice of the methods of the disclosure.

In an exemplary method, the antibodies may be incubated with the sample for a time to form complexes with the TIL cell marker (e.g., CD8). The complexes are then visualized by treating the sections with a stain including, for example, diaminobenizidine (DAB) stain under appropriate conditions. In a second step, the tissue may be counterstained with another optical enhancement factor, for example hematoxylin. Although a staining technique using peroxidase and ethyl green is exemplary, other stains and optical enhancement factors are also suitable such as alkaline phosphatase based with specific chromagens such as Fast Red, Fast Green, etc. Spectral studies have shown that the ethyl green stain offers spectral separation from the DAB precipitate of the immunoperoxidase technique such that different features of the image can be readily separated by filtering it at two different wavelengths. This allows the image to be digitized into two separate images, one in which all the cell nuclei are optically enhanced (hematoxylin or Fast Green) and one in which only those tissue areas with receptor staining (DAB) are optically enhanced.

Following immunohistochemical staining, the optical image of the tissue or cell sample generated by the computer-aided image analysis system may then be magnified under a light microscope and separated into a pair of images. Such equipment can include a light or fluorescence microscope, and image-transmitting camera and a view screen, most preferably also comprising a computer that can be used to direct the operation of the device and store and manipulate the information collected, most preferably in the form of optical density of certain regions of a stained tissue preparation. Image analysis devices useful in the practice of this disclosure include but are not limited to the CAS 200 (Becton Dickenson, Mountain View, Calif.), Chromavision or Tripath systems. The separated images are enhanced using a pair of optical filters, one having a maximum absorption corresponding to the stain and the other having a maximum absorption corresponding to the counterstain. In other embodiments of the method of the present disclosure, a plurality of image analysis filters are used to detect, differentiate, and quantitate the level of staining of different cellular proteins in various components (e.g., membrane, cytoplasm, and nucleus).

After immunohistochemical staining, a quantified measure of the percentage of expressing cells the TIL cell marker can be taken by digitizing microscope images of stained samples, and converting light intensity values in each picture element (pixel) of the digitized image to optical density values, which correspond to the percentage of stained cell nuclei (using image analysis systems such as the system provided by Aperio; Leica Biosystems). More specifically, computerized image analysis can be used to determine from a digital grey scale image, a quantity of cells having a particular stain. The grey scale images are representative of the amount of an optical enhancement factor, such as a chromagen, which binds to a specific target under study and thereby allows optical amplification and visualization of the target.

In practicing the method of the present disclosure, staining procedures can be carried out by a technician in the laboratory. Alternatively, the staining procedures can be carried out using automated systems. In either case, staining procedures for use according to the methods of this disclosure are performed according to standard techniques and protocols well-established in the art.

This disclosure is further illustrated by the following examples which are provided to facilitate the practice of the disclosed methods. These examples are not intended to limit the scope of the disclosure in any way.

EXAMPLES

Example 1: Calculation of irScore

The irScore is calculated from targeted RNA-seq data (immune panel RNA-seq). RNA-seq analysis was performed on a non-small cell lung cancer (NSCLC) tissue. The RNA-seq assay measures the expression levels of certain genes including immune-related genes (Table 1).

Figure 1B:
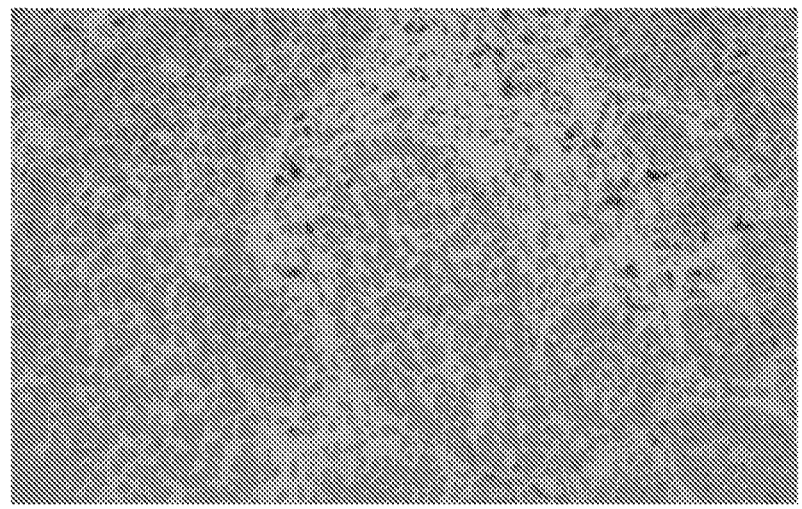
Figure 1C:
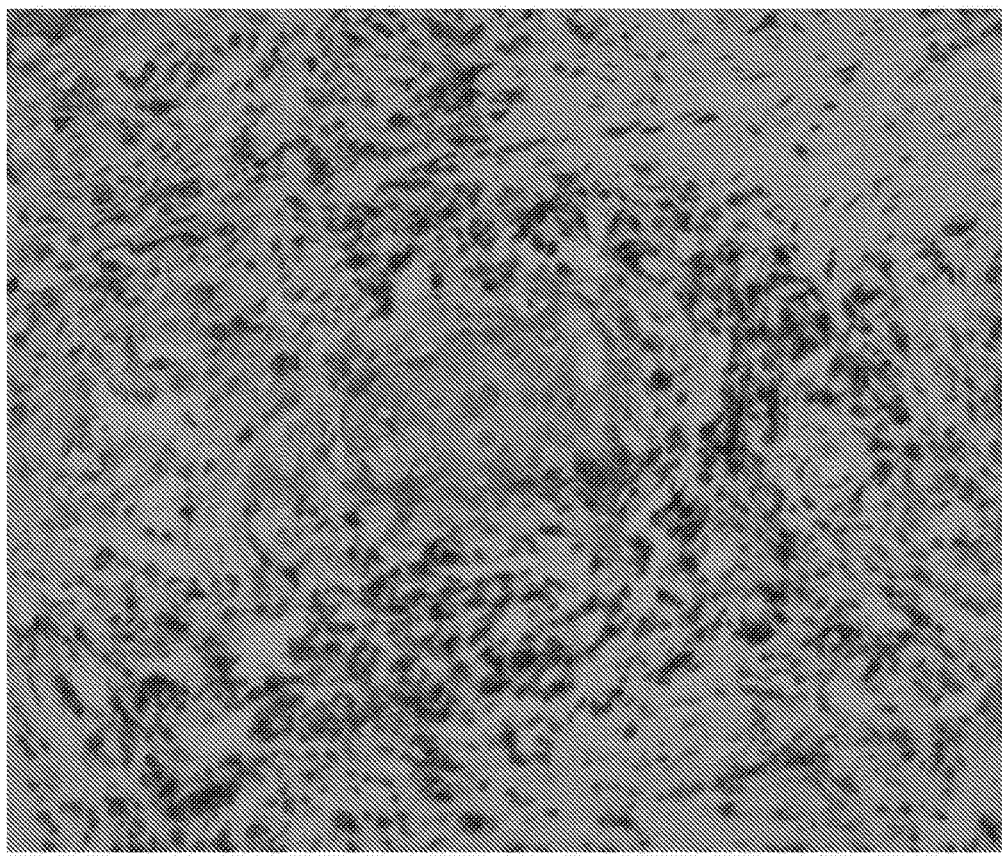

Prior to the RNA-seq assay, each NSCLC tissue was classified into groups based on the level of immune infiltration in each tissue (high immune infiltration versus low immune infiltration; see, FIG. 1). Following tissue classification, the expression levels of the genes in Table 1 were used to generate gene expression values for NSCLC tumors with high levels of immune infiltration, and NSCLC tumors with low levels of immune infiltration. The comparison of RNA-seq data between NSCLC tumors (immune infiltrate "high" tumors versus immune infiltrate "low" tumors) revealed a gene expression signature that is associated with immune cell infiltration and aggregation.

The gene expression profiles underwent bioinformatics analysis to identify statistically significant gene expression differences between NSCLC tissue from immune infiltrate "high" tumors versus immune infiltrate "low" tumors.

The irScore relies on determining the total number of differentially expressed genes (i.e., between immune infiltrate "high" tumors versus immune infiltrate "low" tumors) from the RNA-seq immune panel, with a focus on the expression of genes that promote or inhibit an anti-tumor immune response. In this manner, the irScore accounts for the expression of genes that contribute (or are hypothesized to contribute) to the anti-tumor immune response, and the irScore also accounts for the expression of immunosuppressive genes (or genes hypothesized to be immunosuppressive genes).

The gene expression analysis revealed that 88 genes (of those genes set forth in Table 1) are differentially expressed (at least an approximately 2-fold difference) between NSCLC tumors (Immune infiltrate "high" tumors vs immune Infiltrate "low" tumors). The list of 88 genes was then classified into functional groups based on their role in immune cell signaling: "Immune Activity" or "Immunosuppression" if known (Table 2). Genes that have unknown roles in immune cell signaling were not counted.

TABLE 2

Gene signature associated with immune infiltration and immune cell aggregation

| 88 Immune gene signature | "Immune Active" | "Immuno-suppression" | Stimulate and/or suppress Immune response* |
|---|---|---|---|
| ACTB | | | |
| APOL3 | | | |
| ARHGEF2 | 1 | | |
| ARID1A | | | |
| ARID1B | | | |
| CA9 | | | |
| CCL18 | ? | ? | 1 |
| CCL19 | 1 | | |
| CCL4 | 1 | | |
| CCL7 | 1 | | |
| CCR10 | 1 | | |
| CCR2 | 1 | | |
| CCR5 | 1 | | |
| CD27 | 1 | | |
| CD38 | 1 | | |
| CD3D | | | |
| CD3E | 1 | | |
| CD5 | | 1 | |
| CD63 | ? | ? | 1 |
| CD7 | ? | ? | 1 |
| CD70 | | ? | 1 |
| CD8A | 1 | | |
| CD8B | 1 | | |
| CEBPB | | | |
| CRTAM | ? | ? | 1 |
| CSF1 | ? | ? | 1 |
| CTLA4 | | 1 | |
| CXCL1 | | | |
| CXCL10 | 1 | | |
| CXCL11 (ITAC) | | | |
| CXCL2 | | | |
| CXCL6 | | | |
| CXCL9 (MIG) | | | |
| CXCR1 | | | |
| CXCR2 | | | |
| CXCR7 | | | |
| EOMES | ? | ? | 1 |
| FASLG | ? | ? | 1 |
| FGL2 | | 1 | |
| FLT3 | 1 | | |
| GBP1 | 1 | | |
| GZMA | 1 | | |
| GZMB | 1 | | |
| GZMH | 1 | | |
| HAVCR2 | | 1 | |
| HLA-B | 1 | | |
| HLA-C | 1 | | |
| HLA-E | 1 | | |
| IDO1 | | 1 | |
| IFNGR1 | | | |
| IL10RA | | 1 | |
| IL11RA | | | |
| IL12RB1 | 1 | | |

TABLE 2-continued

Gene signature associated with immune infiltration and immune cell aggregation

| 88 Immune gene signature | "Immune Active" | "Immuno-suppression" | Stimulate and/or suppress Immune response* |
|---|---|---|---|
| IL16 | | | |
| IL22RA1 | | | |
| IL33 | | | |
| IL3RA | 1 | | |
| IRF1 | 1 | | |
| IRF8 | 1 | | |
| IRF9 | | 1 | |
| ITM2A | | | |
| KITLG | | | |
| LTBR | 1 | | |
| MAGEC2 | | | |
| MAGED2 | 1 | | |
| MAGEF1 | | | |
| MET | | | |
| MICA | 1 | | |
| MSH2 | | | |
| MSH6 | | | |
| NCK1 | 1 | | |
| NFATC1 | ? | ? | 1 |
| NFATC4 | 1 | ? | |
| PDCD1LG2 (PD-L2; PDL2) | | | |
| PRF1 | 1 | | |
| RRM1 | | | |
| SOCS1 | | | |
| SPP1 | | | |
| STAT1 | 1 | | |
| TLR3 | | | |
| TNFRSF14 | ? | ? | 1 |
| TNFRSF25 | ? | ? | 1 |
| TNFSF13B | 1 | | |
| TNFSF15 | | | |
| TNFSF9 | 1 | | |
| TOP2A | | | |
| TRADD | 1 | | |
| VTCN1 (B7-T4) | | | |
| Total | 35 | 7 | 11 |

Note:
Specific genes may have putative roles in both "Immune Activity" and "Immunosuppression".
All expression data is normalized as Reads Per Kilobase per Million mapped reads.

The irScore is then calculated by determining the number of differentially expressed genes in either the "Immune Activity" category or "Immunosuppression" category (e.g., as shown in Table 2 above). Differential expression is determined by comparison of the gene expression data in the "test sample" to the gene expression data in a "reference" sample. The irScore may be calculated as follows:

$$\text{irScore} = X^{(low,\ medium,\ or\ high)},$$

where X=# of differentially expressed genes that function in anti-tumor immune cell signaling/activation, and where "low", "medium", and "high" refer to the # of differentially expressed genes that contribute to immunosuppression (e.g., low=1-4 genes; Medium=5-9 genes; High=10+ genes)

In the example shown in Table 2, 35 "Immune Activity" genes are differentially expressed between the NSCLC "test tissue" and the "reference tissue". Therefore, X=35 genes (see, Table 2). Further, in the example shown in Table 2, 7 "immunosuppression" genes are differentially expressed between the NSCLC "test tissue" and the "reference tissue". Therefore, the "immunosuppression" value is 7 genes, which corresponds to "medium" suppression (see, Table 2). In summary, the complete irScore=$35^{(medium)}$, corresponds to the differential expression of 35 "Immune Activity" and 7 "Immunosuppression" genes and indicates the this tumor is responsive to an anti-cancer immunotherapy.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method for treating a subject with an anticancer immunotherapy, the method comprising:
    (a) obtaining a biological sample from the subject;
    (b) determining a number of expressed genes that are implicated in anti-tumor immune cell signaling/activation in a biological sample;
    (c) determining a number of expressed genes that are implicated in immunosuppression in the biological sample; and
    (d) calculating an irScore from the determinations of (b) and (c), wherein the irScore=$X^{(low,\ medium,\ or\ high)}$, wherein X is the number of expressed genes that are implicated in anti-tumor immune cell signaling/activation, and wherein low refers to 1-4 expressed genes that are implicated in immunosuppression, medium refers to 5-9 expressed genes that are implicated in immunosuppression, and high refers to 10 or more expressed genes that are implicated in immunosuppression; and
    (e) treating the subject with the immunotherapy where the irScore is at least $5^{low}$, $6^{low}$, $7^{low}$, $8^{low}$, $9^{low}$, $10^{low}$, $11^{low}$, $12^{low}$, $13^{low}$, $14^{low}$, $15^{low}$, $16^{low}$, $17^{low}$, $18^{low}$, $19^{low}$, $20^{low}$, $21^{low}$, $22^{low}$, $23^{low}$, $24^{low}$, or $25^{low}$ or greater, $5^{medium}$, $6^{medium}$, $7^{medium}$, $8^{medium}$, $9^{medium}$, $10^{medium}$, $11^{medium}$, $12^{medium}$, $13^{medium}$, $14^{medium}$, $15^{medium}$, $16^{medium}$, $17^{medium}$, $18^{medium}$, $19^{medium}$, $20^{medium}$, $21^{medium}$, $22^{medium}$, $23^{medium}$, $24^{medium}$, or $25^{medium}$ or greater, or at least $5^{high}$, $6^{high}$, $7^{high}$, $8^{high}$, $9^{high}$, $10^{high}$, $11^{high}$, $12^{high}$, $13^{high}$, $14^{high}$, $15^{high}$, $16^{high}$, $17^{high}$, $18^{high}$, $19^{high}$, $20^{high}$, $21^{high}$, $22^{high}$, $23^{high}$, $24^{high}$, or $25^{high}$ or greater.

2. The method of claim 1, wherein the subject is a cancer patient.

3. The method of claim 1, wherein the anticancer immunotherapy is Nivolumab, Pembrolizumab, Atezolizumab, Durvalumab, Avelumab, Ipilimumab, or Tremelimumab.

4. The method of claim 1, wherein the biological sample is non-small cell lung cancer (NSCLC).

5. The method of claim 1, wherein the expressed genes that are implicated in anti-tumor immune cell signaling/activation are selected from subset of genes set forth in Table 2.

6. The method of claim 1, wherein the expressed genes that are implicated in immunosuppression are selected from subset of genes set forth in Table 2.

7. The method of claim 1, wherein the expressed genes that are implicated in anti-tumor immune cell signaling/activation are selected from subset of genes set forth in Table 2 and wherein the expressed genes that are implicated in immunosuppression are selected from subset of genes set forth in Table 2.

8. The method of claim 1, wherein the expressed genes that are implicated in anti-tumor immune cell signaling/activation are selected from those genes set forth in Table 1.

9. The method of claim 1, wherein the expressed genes that are implicated in immunosuppression are selected from those genes set forth in Table 1.

10. The method of claim 1, wherein the expressed genes that have are implicated in anti-tumor immune cell signaling/activation are selected from those genes set forth in Table 1 and wherein the expressed genes that are implicated in immunosuppression are selected from those genes set forth in Table 1.

\* \* \* \* \*